(12) United States Patent
McAuley

(10) Patent No.: US 8,479,726 B2
(45) Date of Patent: Jul. 9, 2013

(54) BREATHING ASSISTANCE APPARATUS

(75) Inventor: Alastair Edwin McAuley, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 1187 days.

(21) Appl. No.: 12/300,563

(22) PCT Filed: Jun. 7, 2007

(86) PCT No.: PCT/NZ2007/000141
§ 371 (c)(1),
(2), (4) Date: Dec. 11, 2008

(87) PCT Pub. No.: WO2007/145534
PCT Pub. Date: Dec. 21, 2007

(65) Prior Publication Data
US 2009/0107504 A1   Apr. 30, 2009

(30) Foreign Application Priority Data
Jun. 16, 2006   (NZ) .......................................... 547973

(51) Int. Cl.
*A61M 16/06* (2006.01)

(52) U.S. Cl.
USPC ............ 128/201.17; 128/200.24; 128/201.11; 128/200.26

(58) Field of Classification Search
USPC .............. 128/200.24, 201.11, 201.17, 200.26
See application file for complete search history.

(56) References Cited

U.S. PATENT DOCUMENTS

| | | | |
|---|---|---|---|
| 5,243,971 A | 9/1993 | Sullivan et al. | |
| 6,112,746 A | 9/2000 | Kwok et al. | |
| 6,736,139 B1 | 5/2004 | Wix | |
| 2003/0019496 A1 | 1/2003 | Kopacko et al. | |
| 2004/0182398 A1 | 9/2004 | Sprinkle et al. | |
| 2005/0199239 A1 | 9/2005 | Lang et al. | |

FOREIGN PATENT DOCUMENTS

| | | |
|---|---|---|
| AU | 2003246441 | 12/2003 |
| EP | 1099452 | 5/2001 |
| WO | WO 02/11804 | 2/2002 |
| WO | 2006/074513 | 7/2006 |
| WO | 2006/074514 | 7/2006 |
| WO | 2007/009182 | 1/2007 |

OTHER PUBLICATIONS

Australian Examination Report; dated Aug. 16, 2012; 6 pages.

*Primary Examiner* — Jerome W Donnelly
(74) *Attorney, Agent, or Firm* — Knobbe, Martens, Olson & Bear, LLP

(57) ABSTRACT

The breathing assistance apparatus has a patient interface with a body section adapted to cover the nose, or nose and mouth of the patient. The apparatus includes a sealing interface, including at least an outer sealing member. The outer sealing member has a periphery that is attached to the body section in a sealing manner. The periphery is substantially rigid compared to the remainder of the outer sealing member. The outer sealing member is adapted to substantially seal around the facial contours of the patient to provide a sealed fluid communication to the respiratory tract of the patient. The sealing interface may also include an inner sealing member.

17 Claims, 16 Drawing Sheets

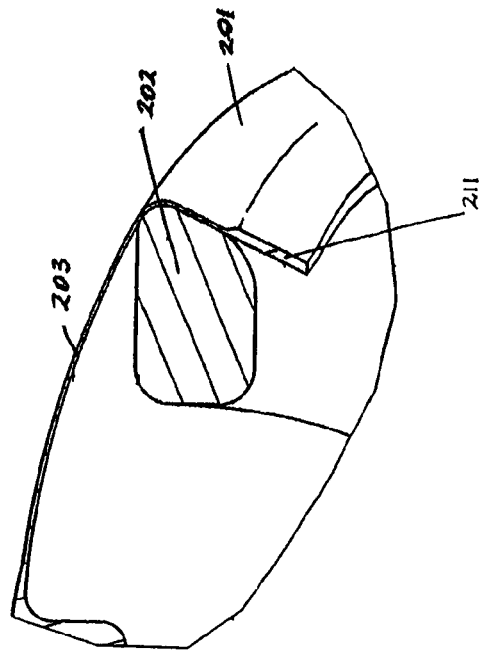
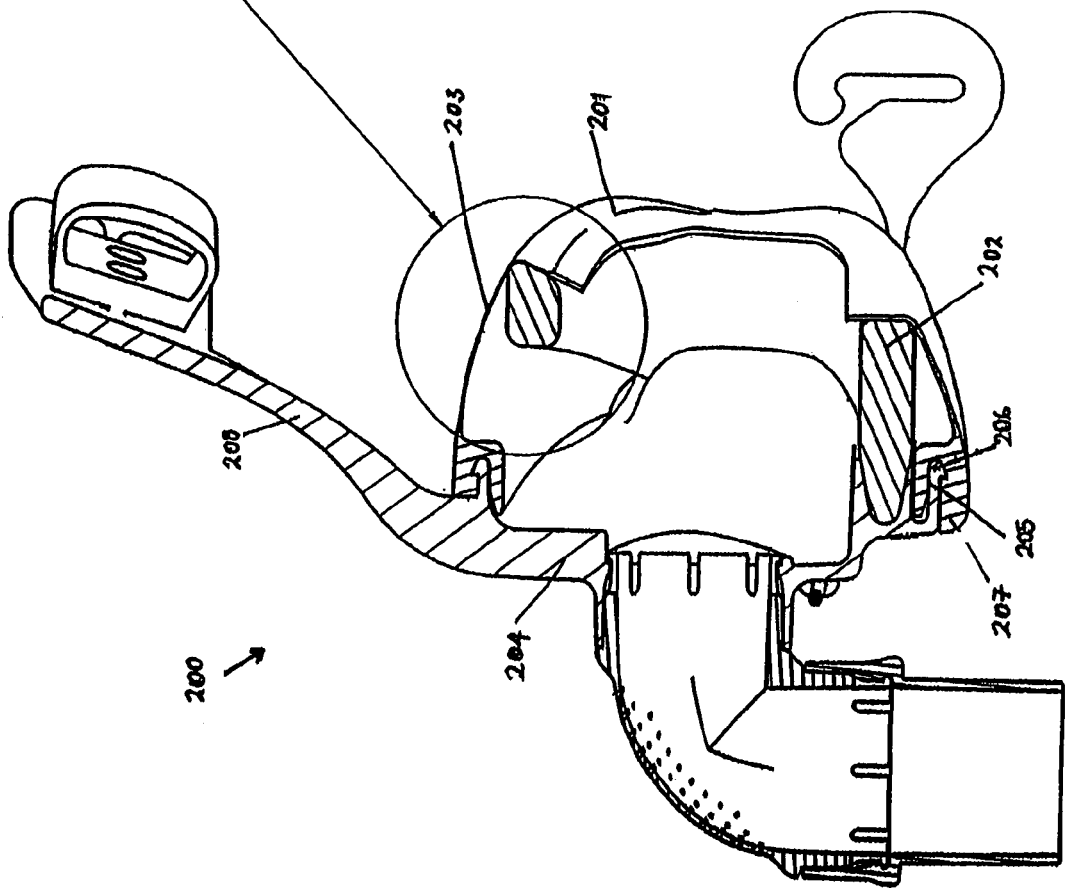
Figure 13
Figure 12

BREATHING ASSISTANCE APPARATUS

This application is a National Phase filing of PCT/NZ2007/000141, having an International filing date of Jun. 7, 2007, which disclosure is herein incorporated by reference.

TECHNICAL FIELD

This invention relates to patient interfaces particularly though not solely for use in delivering CPAP therapy to patients suffering from obstructive sleep apnoea (OSA). In particular this invention relates to cushions for use with patient interfaces.

BACKGROUND ART

In the art of respiration devices respiratory masks which cover the nose and/or mouth of a human user are known. Known masks provide a continuous seal around the nasal and/or oral areas of the face, such that gas may be provided at positive pressure within the mask for consumption by the user. The uses for such masks range from high altitude breathing (i.e., aviation applications) to mining and fire fighting applications, to various medical diagnostic and therapeutic applications.

One requisite of such respiratory masks is to provide an effective seal against the user's face to prevent leakage of the gas being supplied. Commonly, in prior mask configurations, a good mask-to-face seal has been attained in many instances only with considerable discomfort for the user. A common complaint of a user of CPAP therapy is pressure sores caused by the mask about the nose and face and in particular in the nasal bridge region of the user. This problem is most crucial in those applications, especially medical applications, which require the user to wear such a mask continuously for hours or perhaps even days. In such situations, the user will not tolerate the mask for long durations and optimum therapeutic or diagnostic objectives may often not be achieved, or will be achieved with great difficulty and considerable user discomfort.

U.S. Pat. Nos. 5,243,971 and 6,112,746 are examples of prior art attempts to improve patient interfaces.

DISCLOSURE OF THE INVENTION

It is an object of the present invention to attempt to provide a patient interface which goes some way to overcoming disadvantages in the prior art or which will at least provide the industry with a useful choice.

Accordingly the present invention consists in a breathing assistance apparatus, for use with delivery of respiratory gases to a patient comprising:

a patient interface, having a body section adapted to cover the nose, or nose and mouth of said patient, a sealing interface, including at least an outer sealing member, said outer sealing member having a periphery that is attachable to said body section in a sealing manner, said periphery being substantially rigid compared to the remainder of said outer sealing member, wherein said outer sealing member is adapted to substantially seal around the facial contours of said patient providing a sealed fluid communication to the respiratory tract of said patient.

Preferably said body section includes a ridge to receive said periphery of said sealing interface.

Preferably said ridge includes protrusions that assist in the friction engagement of said sealing interface to said body section.

Preferably said periphery includes protrusions that assist in a friction or snap engagement of said sealing interface to said body section.

Preferably said patient interface is a full face mask.

Preferably said outer sealing member has a substantially thin section in at least its nasal bridge region, said thin section being substantially thinner than the remainder of said outer sealing member.

Preferably said outer sealing member includes a second thin section in the region where said outer sealing member rests against the chin of said patient in use, said second thin section being substantially thinner than the remainder of said outer sealing member.

Alternatively said patient interface is a nasal mask.

Preferably said outer sealing member has a substantially thin section in at least its nasal bridge region, said thin section being substantially thinner than the remainder of said outer sealing member.

Preferably said sealing interface includes an inner sealing member fittable into said outer sealing member.

Preferably said inner sealing member has a cut out region in the nasal bridge region.

Preferably said inner sealing member has a cut out region in the cheek region.

Preferably said inner sealing member has a cut out region in the upper lip region.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

The invention consists in the foregoing and also envisages constructions of which the following gives examples.

BRIEF DESCRIPTION OF THE DRAWINGS

Preferred forms of the present invention will now be described with reference to the accompanying drawings.

FIG. 12 is a side view of a nasal mask of the present invention where the outer sealing member is substantially thinner in width in the nasal bridge region than the rest of the outer sealing member.

FIG. 13 is a close-up view of detail A in FIG. 12.

DESCRIPTION OF THE PREFERRED EMBODIMENTS OF THE INVENTION

The sealing interface of the present invention provides improvements in the delivery of CPAP therapy. It will be appreciated that the patient interface as described in the preferred embodiment of the present invention can be used in respiratory care generally or with a ventilator but will now be described below with reference to use in a humidified CPAP system. It will also be appreciated that the present invention can be applied to any form of patient interface including, but not limited to nasal masks, oral masks and mouthpieces.

Figure 1:
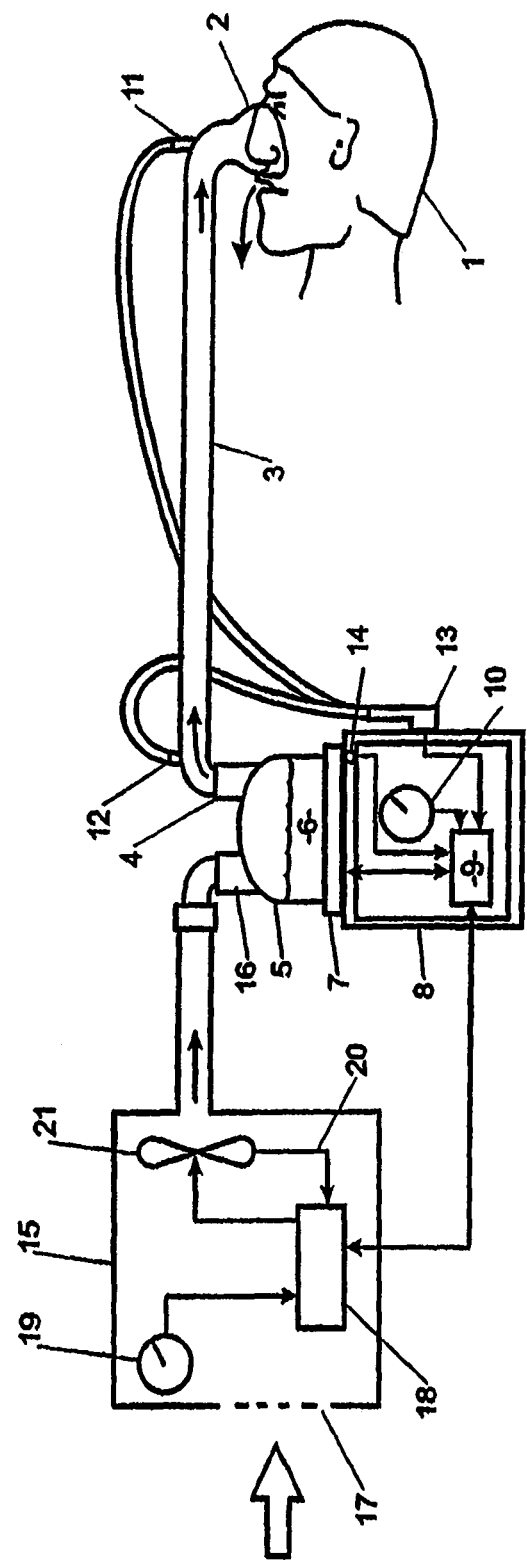
FIG. 1 is a block diagram of a humidified continuous positive airway pressure (system) as might be used in conjunction with the sealing interface of the present invention.

With reference to FIG. 1 a humidified Continuous Positive Airway Pressure (CPAP) system is shown where a patient 1 is receiving humidified and pressurised gases through a patient interface 2. The interface 2 is connected to a humidified gases transportation pathway or inspiratory conduit 3. It should be understood that delivery systems could also be VPAP (Variable Positive Airway Pressure) and BiPAP (Bi-level Positive Airway Pressure) or numerous other forms of respiratory therapy. The inspiratory conduit 3 is connected to an outlet 4 of a humidification chamber 5 that contains a volume of water 6. The inspiratory conduit 3 may contain heating means or heater wires (not shown) that heat the walls of the conduit to reduce condensation of humidified gases within the conduit. The humidification chamber 5 is preferably formed from a plastics material and may have a highly heat conductive base (for example an aluminium base) that is in direct contact with a heater plate 7 of humidifier 8. The humidifier 8 is provided with control means or an electronic controller 9, which may comprise a microprocessor based controller executing computer software commands stored in associated memory.

The controller 9 receives input from sources such as user input means or a dial 10 through which a user of the device may, for example, set a predetermined required value (preset value) of humidity or temperature of the gases supplied to patient 1. The controller 9 may also receive input from other sources, for example temperature and/or flow velocity sensors 11, 12, through a connector 13 and a heater plate temperature sensor 14. In response to the user set humidity or temperature value input via the dial 10 and the other inputs, the controller 9 determines when (or to what level) to energise the heater plate 7 to heat the water 6 within the humidification chamber 5. As the volume of the water 6 within the humidification chamber 5 is heated, water vapour begins to fill the volume of the chamber above the water's surface and is passed out of the humidification chamber 5 outlet 4 with the flow of gases (for example air) provided from a gases supply means or blower 15 that enters the chamber 5 through an inlet 16. Exhaled gases from the patient's mouth are passed directly to the ambient surroundings.

The blower 15 is provided with variable pressure regulating means or variable speed fan 21 that draws air or other gases through a blower inlet 17. The speed of the variable speed fan 21 is controlled by an electronic controller 18, or alternatively the function of the controller 18 may carried out by the controller 9. The speed is controlled in response to inputs from the controller 9 and a user set predetermined required value (preset value) of pressure or the fan speed via dial 19.

Nasal Mask

Figure 2:
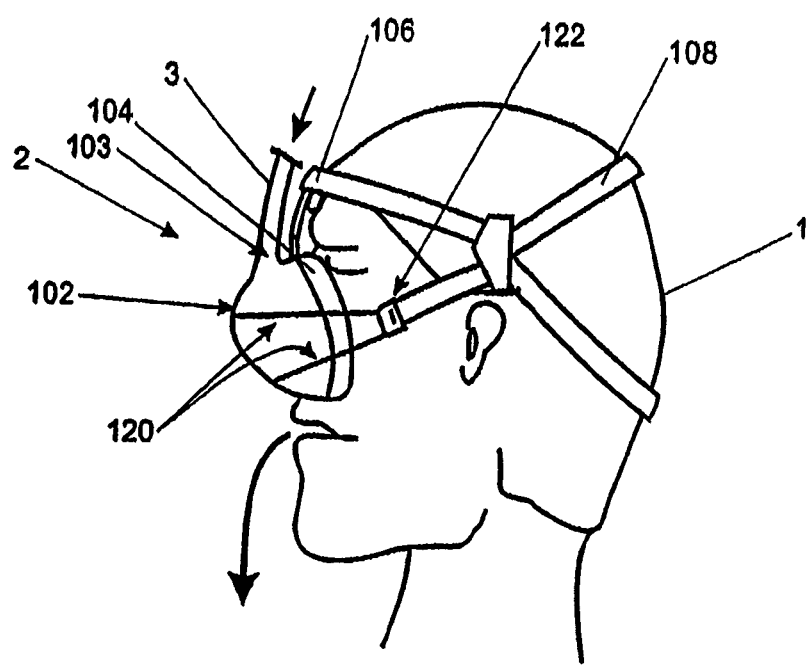
FIG. 2 is an illustration of a nasal mask including a sealing interface in use according to the preferred embodiment of the present invention.

According to a first embodiment of the present invention the patient interface is shown in FIG. 2 as a nasal mask. The mask includes a hollow body 102 with an inlet 103 connected to the inspiratory conduit 3. The mask 2 is positioned around the nose of the patient 1 with the headgear 108 secured around the back of the head of the patient 1. The restraining force from the headgear 108 on the hollow body 102 and the forehead rest 106 provides compressive force on the mask cushion 104 to provide a seal against the patient's face.

The hollow body 102 is constructed of a relatively inflexible material for example, polycarbonate plastic. Such a material would provide the requisite rigidity as well as being transparent and a relatively good insulator. The expiratory gases can be expelled through a valve (not shown) in the mask, an expiratory conduit (not shown), or any other such method as is known in the art.

Mask Cushion

Figure 3:
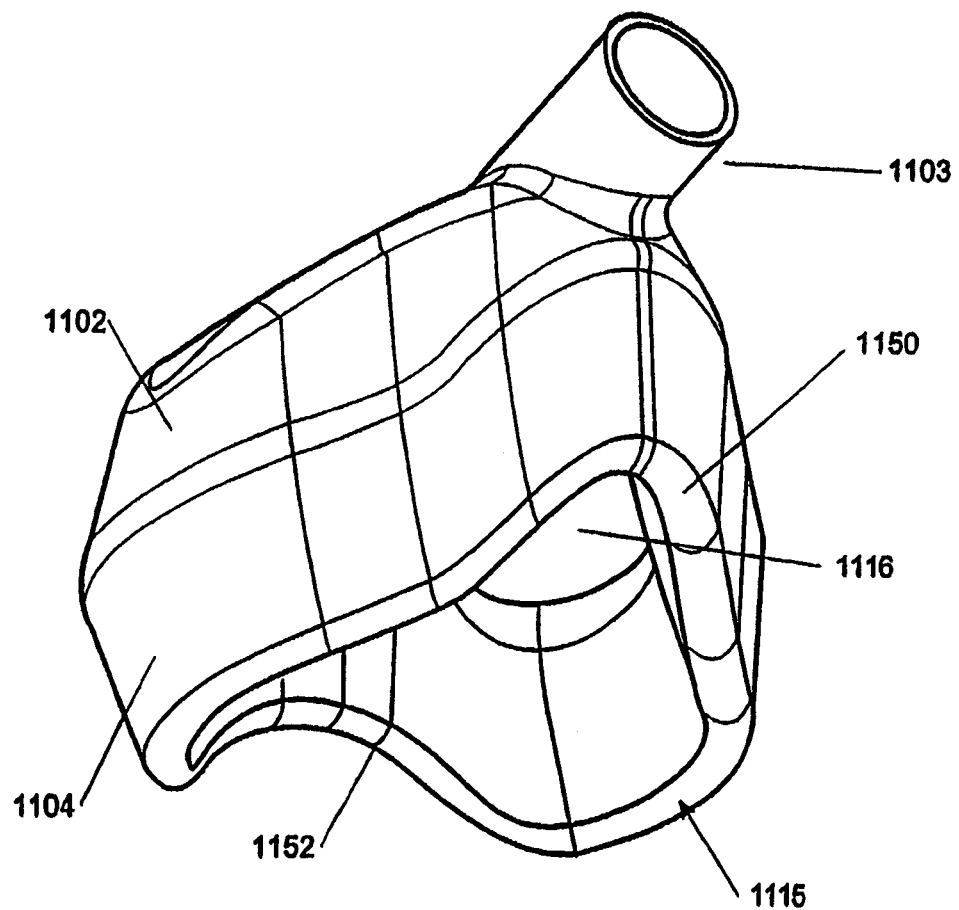
FIG. 3 shows a perspective view of a mask with a sealing interface that is a cushion with an inner sealing member and an outer sealing member.
Figure 4:
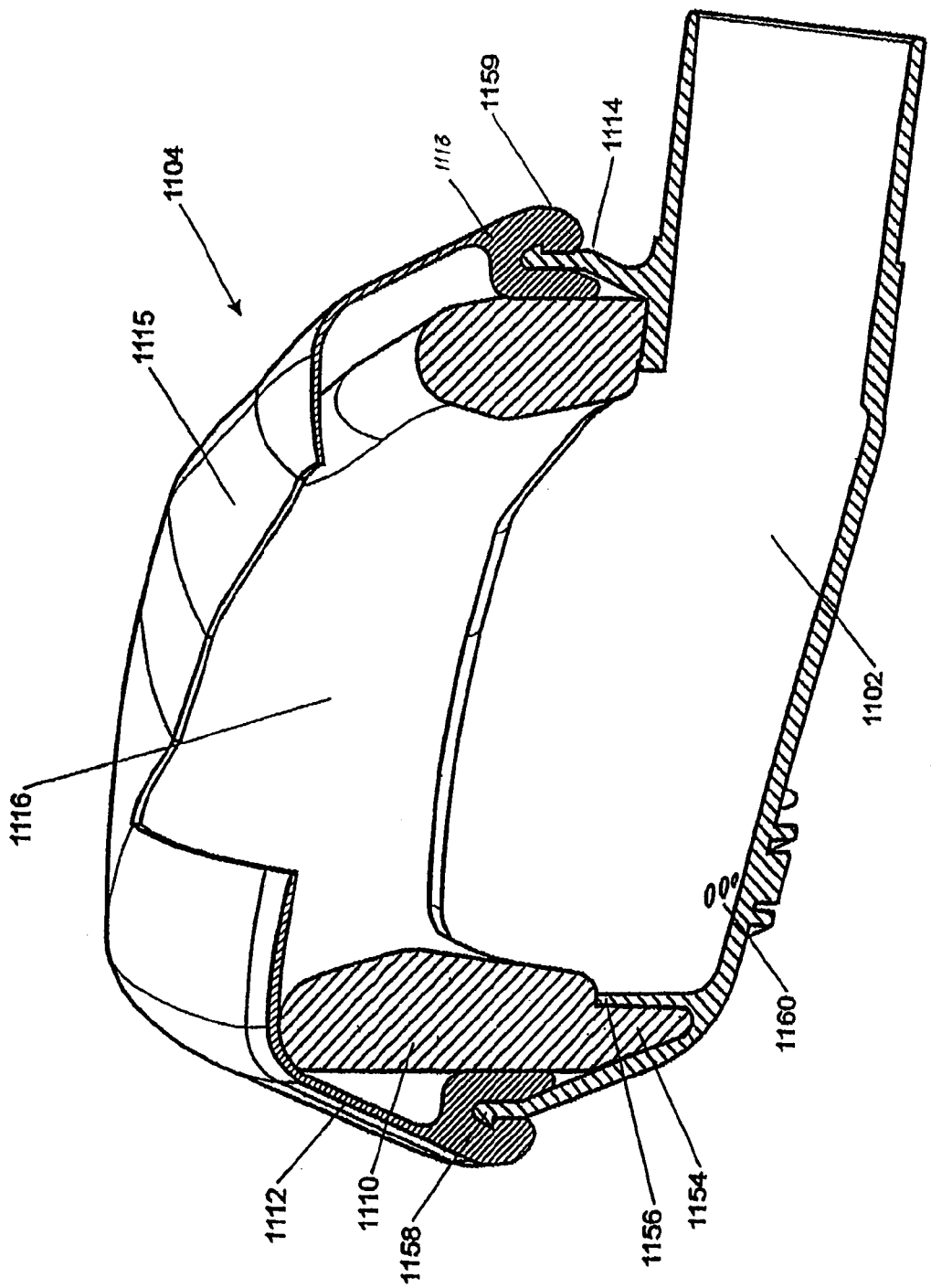
FIG. 4 is a cutaway view of the mask showing the inner sealing member and the outer sealing member of the sealing interface.

One form of the cushion of the patient interface of the present invention will now be described with reference to nasal masks. As shown in FIGS. 3 and 4, a mask cushion 1104 is provided around the periphery of the nasal mask 1102 to provide an effective seal onto the face of the patient to prevent leakage. The mask cushion 1104 is shaped to approximately follow the contours of a patient's face and will deform when pressure is applied by the headgear (not shown) to adapt to the individual contours of any particular patient. In particular, there is an indented section 1150 intended to fit over the bridge of the patient's nose as well as an indented section 1152 to seal around the section beneath the nose and above a user's upper lip.

In FIG. 4 the mask cushion 1104 is composed of an inner cushion 1110 covered by an outer sealing sheath 1112. The inner cushion 1110 is preferably constructed of a resilient material, for example, polyurethane foam, to distribute the pressure evenly along the seal around the patient's face. In other forms the inner cushion may be made of a gel material, such as a silicone gel, or other appropriate soft but resilient material. The inner cushion 1110 is located in use around the outer periphery 1114 of the open face 1116 of the hollow body 1102. Similarly the outer sheath 1112 may be commonly attached at its base 1113 to the periphery 1114 and loosely covers over the top of the inner cushion 1110.

Figure 5:
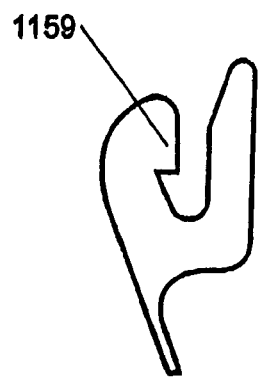
FIG. 5 is a cutaway view of the periphery of the outer sealing member of FIG. 4.
Figure 6:
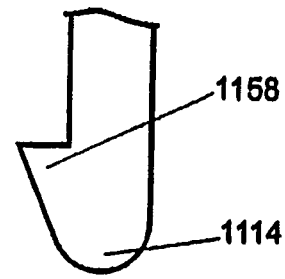
FIG. 6 is a cutaway view of the periphery of the nasal mask body portion of FIG. 4.

In the preferred embodiment of the present invention the bottom of the inner cushion 1110 fits into a generally triangular cavity 1154 in the hollow body 1102, see FIGS. 4 to 6. The cavity 1154 is formed from a flange 1156 running midway around the interior of the hollow body.

The outer sheath 1112 fits in place over the cushion 1110, holding it in place. The sheath 1112 is secured by a snap-fit to the periphery 1114 of the hollow body. In FIGS. 5 and 6 the periphery 1114 is shown including an outer bead 1158. The sheath 1112 includes a matching bead 1159, whereby once stretched around the periphery; the two beads engage to hold the sheath in place.

Figure 8:
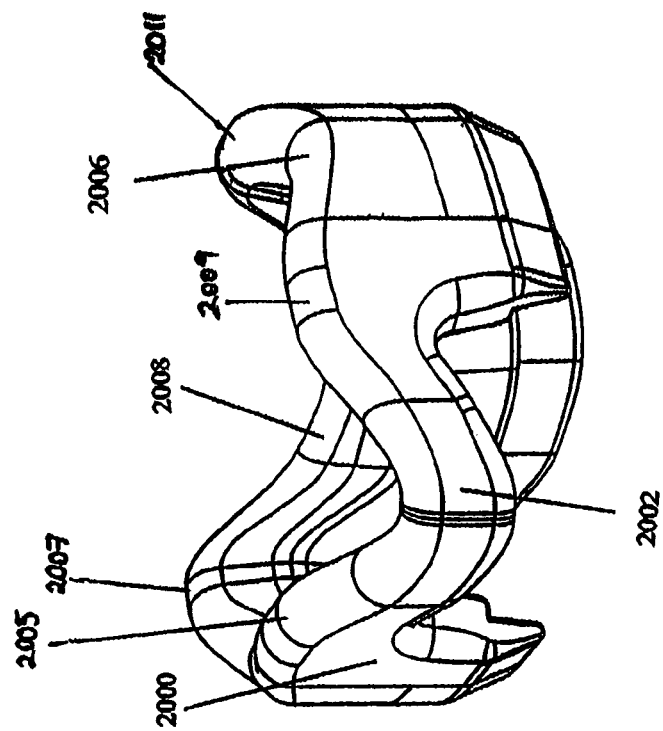
FIG. 8 shows perspective view of an inner sealing member of the second preferred embodiment of the sealing interface.
Figure 7:
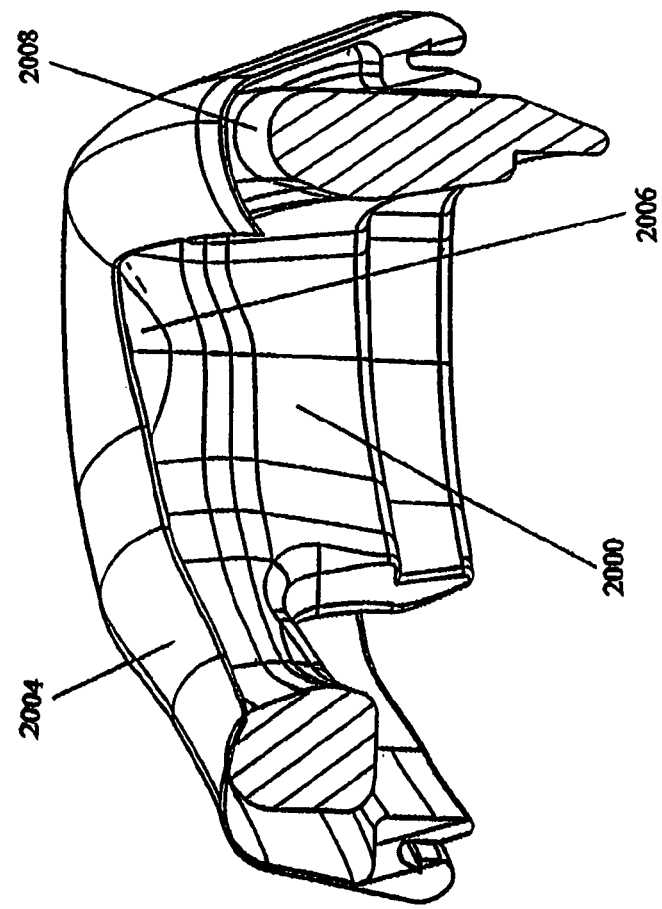
FIG. 7 shows a cross section of a second preferred embodiment of the sealing interface.

A second preferred embodiment to a nasal mask cushion is depicted in FIGS. 7 and 8. In the second embodiment the inner cushion 2000 includes a raised bridge 2002 in the nasal bridge region. The raised bridge 2002 can also be described as a cut out section made in the cushion. Also, the notch in the contacting portion (between the inner cushion and outer sheath) is less pronounced than proceeding embodiments. However, as the raised bridge 2002 is unsupported it is much more flexible and results in less pressure on the nasal bridge of the patient. The outer sheath 2004 contacts the inner cushion 2000 throughout the raised bridge 2002. The peaks 2005, 2007, 2009, 2011 in the inner cushion 2000 between each of the indented sections 2006, 2008 and the raised bridge 2002 contact the outer sheath 2004 and when in use the sheath 2004 contacts the facial contours of the patient in the regions of these peaks.

Referring particularly to FIG. 8 the inner cushion 2000 includes a cheek contour 2006 to follow the cartilage extending from the middle of the nose, and a contoured lip sealing portion 2008 to seal between the base of the nose and the upper lip.

Figure 9:
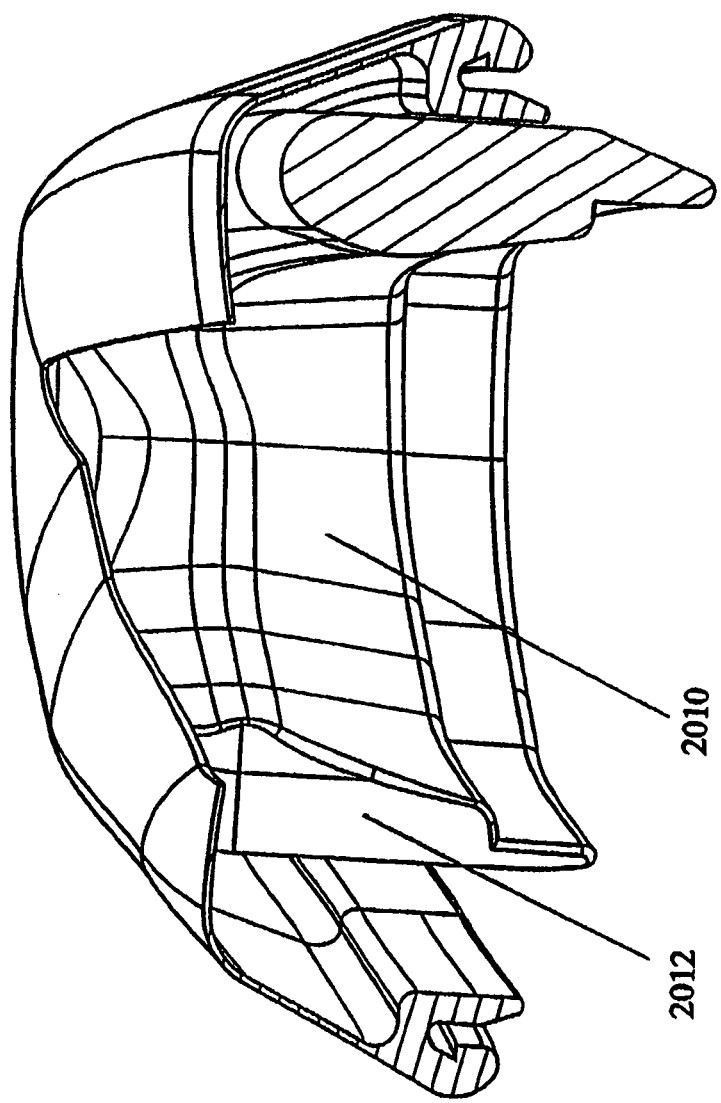
FIG. 9 shows a cross section of a third preferred embodiment of the inner and outer sealing members of the present invention.
Figure 11:
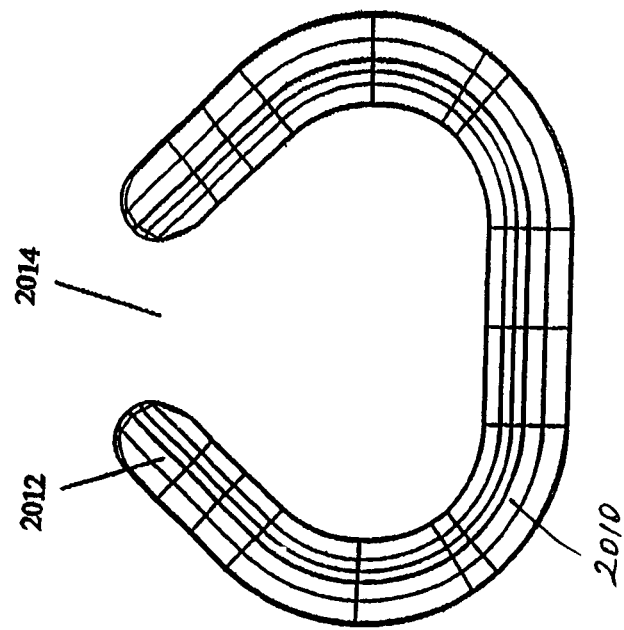
FIG. 11 shows a plan view of the inner sealing member of the third preferred embodiment of the mask cushion.
Figure 10:
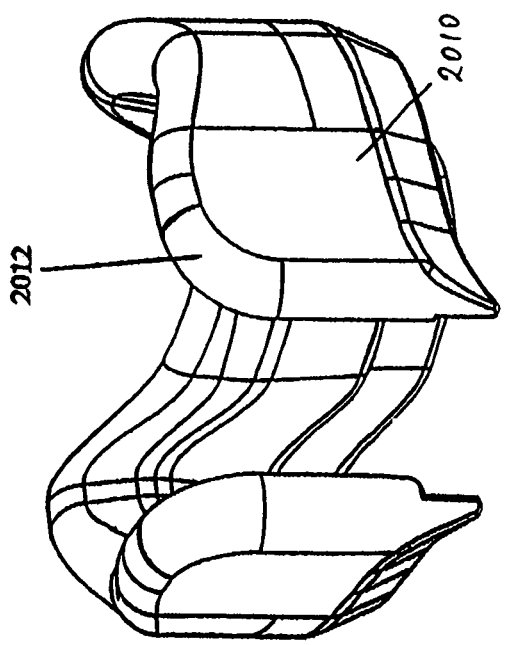
FIG. 10 shows a perspective view of the inner sealing member or cushion of the third preferred embodiment of the sealing interface.

Referring now to FIGS. 9 and 10 a third preferred embodiment of the mask cushion is depicted. In this case, the inner cushion 2010 tapers down 2012 towards the nasal bridge region 2014. For a short portion either side of the nasal bridge region 2014 the inner cushion 2010 is absent, forming a semi annular form in plan view as seen in FIG. 11.

In yet other forms of the sealing interface of the present invention the inner cushion may be provided with other contours on the front side of the inner cushion or cut outs on the back side of the inner cushion, so that in the areas where there are regions cut out of the back side of the cushion the cushion is more flexible. In particular, cut outs in the nasal bridge, cheek and upper lip regions provide the patient with a mask cushion that is more flexible and thus more comfortable.

Referring now to FIG. 12, to improve the comfort to the patient, a nasal mask 200 may include a thin bridge section 203 in the nasal bridge region of the outer sealing member 201, that is, that part extending over the bridge of a patient's nose.

Similar to described above the outer sealing member or outer sheath 201 fits in place over the inner sealing member (inner cushion) 202, holding the inner cushion in place. The outer sheath 201 is secured by a snap-fit to the periphery 205 of the mask hollow body 204. The periphery 205 is shown including an outer bead 206. The outer sheath 201 includes a matching bead 207, whereby once stretched around the periphery 205; the two beads engage to hold the outer sheath 201 in place.

Figure 14:
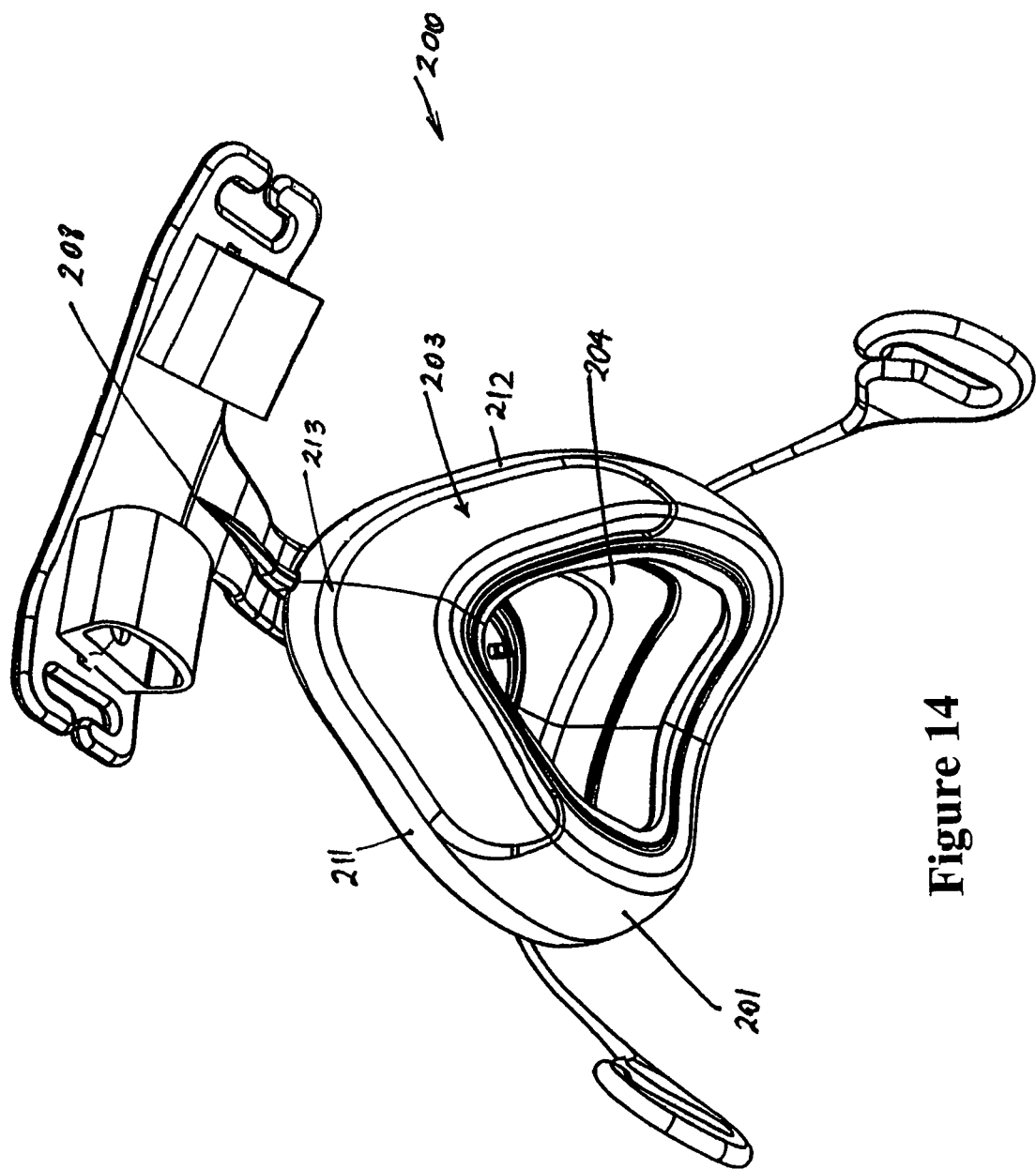
FIG. 14 is a perspective view of the nasal mask of FIG. 12.
Figure 15:
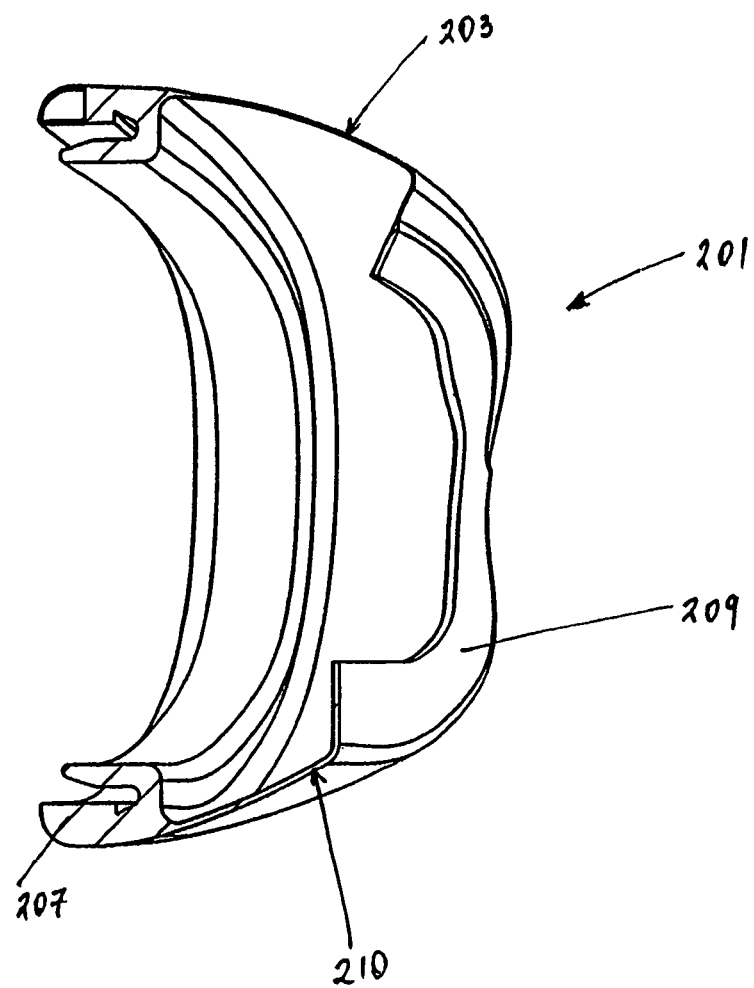
FIG. 15 is a cross-section of the outer sealing member of FIG. 12.

The outer sealing member or sheath 201 is shown in more detail in FIGS. 13 to 15. The outer sheath 201 has formed in it a region 203 than is thinner than the remainder of the cross-sectional thickness 210 of the sheath. In particular, the side walls 211, 212 (see FIG. 14) must be thicker than in the region 203 so as to provide structural support for the sheath and ensure the sheath does not collapse in use, or when being assembled with the mask body. As an example only, for a nasal mask, if the thin bridge region was 0.2 mm thick, the side walls may be 0.3 to 0.6 mm thick. Therefore, the thin bridge region 203 is approximately half the thickness of the rest of the sheath 201 and so can provide a significant effect, such that the pressure to the patient's nose in the nasal bridge region is reduced compared to when a sheath does not have any reduced thickness section. Furthermore, a thin bridge region 203 in the outer sheath 201 allows for different sized patient's to comfortably use the mask and outer sheath of the present invention.

In use, when a force is placed against the outer sheath 201 the thin bridge region 203 will collapse more than the rest of the outer sheath 201. Therefore, this section 203 is more flexible and allows for added patient comfort.

Referring particularly to FIG. 13, the thin bridge region 203 on the outer sheath 201 preferably does not extend completely to the outer edge 211 of the outer sheath 201, but grows gradually thicker. This is because the outer edges of the outer sheath 201 when thicker are less prone to tearing.

In particular, in FIG. 14, that outer sheath 201 is substantially heart shaped and the thin bridge region 203 is shown to extend more than halfway down the sides of the sheath from the apex 213. As shown in FIG. 14, the thin bridge region 203 does not extend fully down the edges 211 and 212 of the outer sheath 201. This is because support is required in the edges of the sheath 201, to provide structural stability of the sheath.

Figure 21:
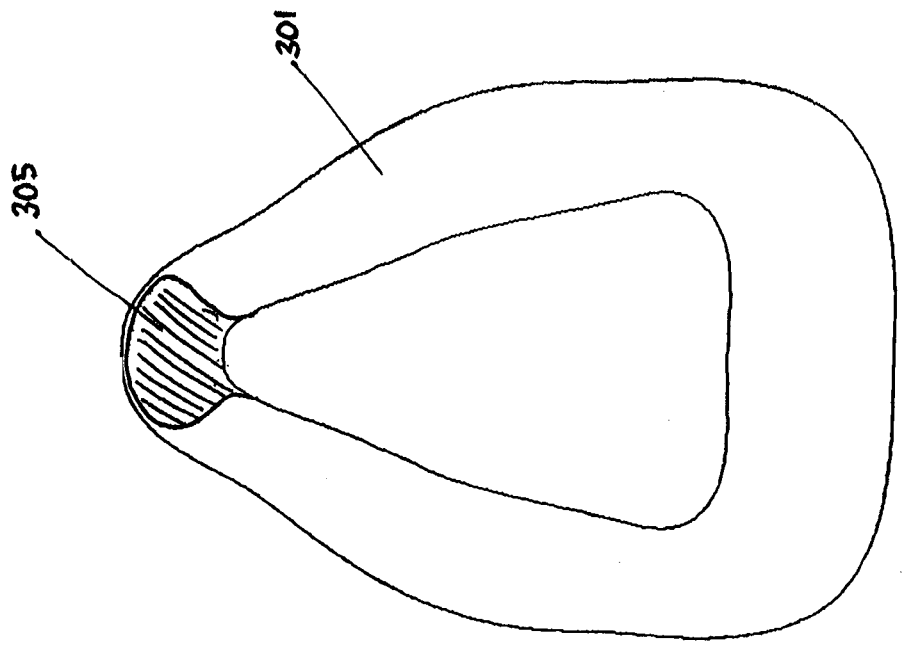
FIG. 21 is a front view of the outer sealing member of FIG. 19.
Figure 20:
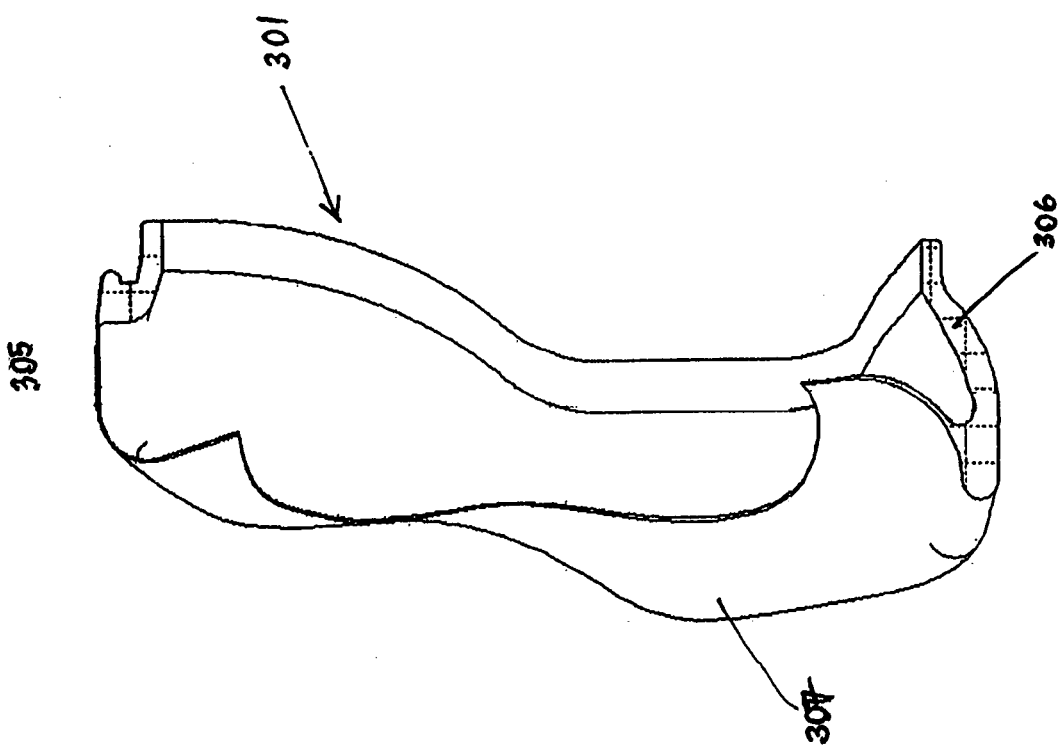
FIG. 20 is a cross-section through CC of the outer sealing member of FIG. 19.

In other forms of the nasal mask of the present invention, the thin bridge region may not extend as far as that shown in FIG. 14, but be restricted merely to the nasal bridge region (similar in manner to the mask cushion shown in FIG. 21, in relation to a full face mask).

Full Face Mask

A further embodiment of the present invention is shown in FIGS. 16 to 21 where the patient interface is a full face mask similar to that described in co-pending New Zealand patent application number 528029. The full face mask 300 includes a hollow body or base 302 and an outer sealing member or mask cushion 301. The cushion 301 is attached to the body 302 in a similar manner as described with reference to the nasal mask. Therefore, thus, the cushion 301 periphery extends over a flange on the mask body.

The hollow body 302 has an integrally formed recess (not shown) in which an insert 304 is fitted into. The recess and insert 304 each have complimentary circular apertures (generally indicated as 305) that form an inspiratory inlet when the insert 304 is placed in the recess. The inlet 304 is capable of being connected to the tubing that forms the inspiratory conduit 3 (as shown on FIG. 1). Gases, supplied to the inspiratory conduit 3 from the CPAP device and humidifier, enter the mask through the apertures 305 and the patient is able to breathe these gases. The mask 300 is positioned around the nose and mouth of the patient and headgear (not shown) may be secured around the back of the head of the patient to assist in the maintaining of the mask on the patient's face. The restraining force from the headgear on the hollow body 302 ensures enough compressive force on the mask cushion 301 to provide an effective seal against the patient's face.

The hollow body 302 and insert 304 are injection moulded in a relatively inflexible material, for example, polycarbonate plastic. Such a material would provide the requisite rigidity for the mask as well as being transparent and a relatively good insulator. The mask cushion 301 is preferably made of a soft plastics material, such as silicone, KRATON™, rubber or similar materials.

The cushion 301 of the mask 300 includes a thin bridge section 305 in the nasal bridge region of the cushion 301, that is, that part extending over the bridge of a patient's nose. As an example, in the region of the thin bridge section 305 the walls of the cushion may be 0.2 to 0.3 mm thick and the rest of the cushion may have a thickness of 1 mm. In particular, the side walls need to be thicker to provide support in the cushion, so that it does not collapse during use or assembly with the mask body. In FIG. 29, this is particularly illustrated, as the section 305 in the nasal bridge region is shown as being much thinner than the rest of the cushion (in particular the bottom side wall region 306, which are much thicker in cross-section).

The inner flange 307 of the cushion 301 that rests against the patient's face is also preferably thinner in section than the side walls of the cushion 301 to provide flexibility to the cushion and thus comfort to the patient. In use, the inner flange 307 is the area of the cushion that seals against the patient's face and the side walls of the cushion provide stability to the cushion 301.

In use, when a force is placed against the cushion 301 the thin bridge section 305 will collapse more than the rest of the cushion 301. Therefore, this section 305 is more flexible and allows for added patient comfort.

Forehead Rest

Figure 16:
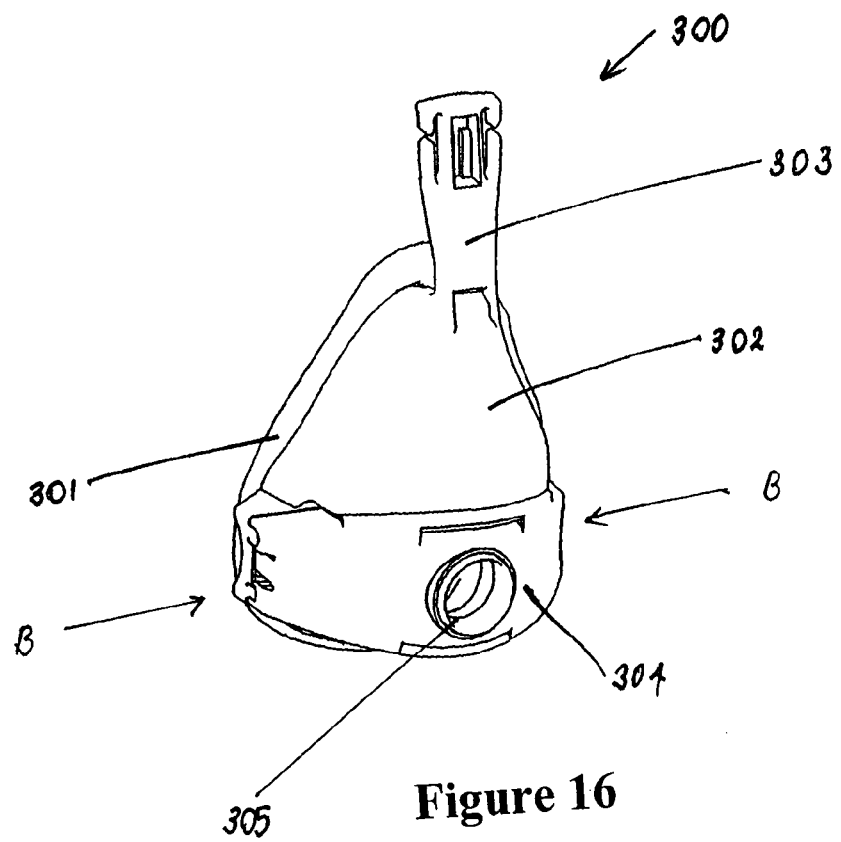
FIG. 16 is a front perspective view of a full face mask of the present invention, where the outer sealing member is substantially thinner in width in the nasal bridge region than the rest of the outer sealing member.

The nasal mask and/or full face mask of the present invention is preferably provided with a fixed forehead rest (208, as shown in relation to the nasal mask in FIGS. 12 and 14 or a rest 303, as shown in relation to the full face mask in FIG. 16). The forehead rest is not required to be adjustable as the cut out in the nasal bridge region of the inner cushion (for the nasal mask) and the thin section in the outer sheath or outer cushion (for both the nasal and full face masks) provides enough flexibility of the mask cushion to provide fitting to a number of different patients.

Rigid Edged Cushion

In one preferred form of the present invention the patient interface has a sealing interface that includes at least an outer sealing member, similar to that described above, with more rigid construction, for example, a rigid edge or periphery, than the prior art. The sealing interface may also include an inner cushion, such as the inner cushion described above. As discussed the inner cushion may be made from foam, silicone or other appropriate type material.

Figure 22:
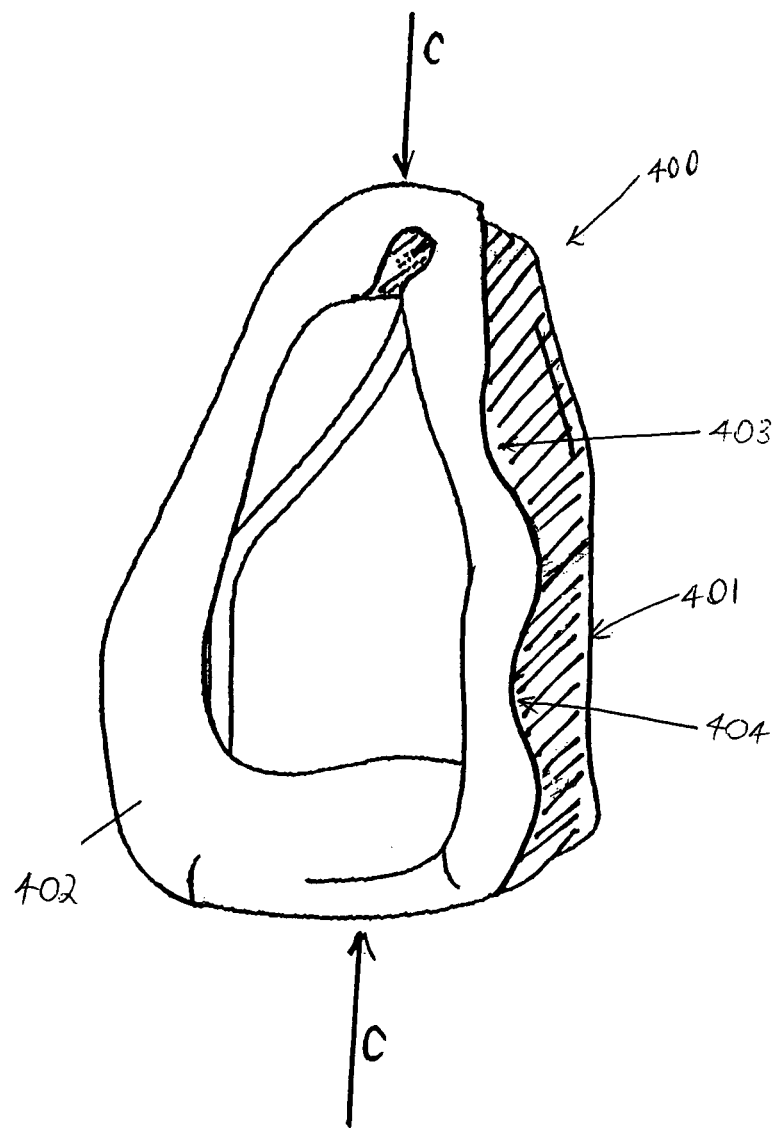
FIG. 22 is a perspective view of a sealing interface of a further embodiment of the present invention where the sealing interface has a substantially rigid periphery.

Referring to FIG. 22 the outer sealing member or outer cushion 400 in this form has a periphery 401 that is attachable to the body section (for example, hollow body or base 302 of the full face mask of FIG. 16) of the patient interface. The periphery 401 is preferably substantially rigid compared to the remainder 402 of the outer cushion. For example, in the preferred form the periphery or edge of the outer cushion may be constructed from silicon and have a hardness of shore A 60 to 80. The remainder of the cushion is constructed from silicone and preferably has a hardness of shore A 3 to 40, this value being considered "soft". However, other materials may be used for the cushion, for example, different grades of thermoplastic, thermoset plastic, thermoplastic polycarbonate nylon, KRATON™ or other similar or appropriate materials.

The periphery 401 comprising a harder or thicker section may vary in width as shown in FIG. 22 where areas of larger width 403, 404 provide additional support in these areas. As an example, areas where additional support might be useful are the parts of the cushion above and below where the cushion rests against a user's cheek in use.

An outer cushion with a rigid periphery would provide the advantage that it would hold its shape more than existing outer cushions, for example those currently sold with the Fisher & Paykel Healthcare Limited FlexiFit™ 405, 407 and 406 Nasal Masks or FlexiFit™ 431 Full Face Mask.

Furthermore, it is anticipated that a sheath with a rigid periphery would be easier to use and would prevent incorrect assembly. With current outer cushions it is possible a user could stretch the outer cushion and attach it incorrectly to the patient interface body. Ensuring correct assembly will ensure the interface and cushion will more reliably stay on the user's face. Consequently, this would ensure correct performance of the interface.

Finally, the softer part of the cushion that rests against the user's face may provide additional user comfort as it will be more flexible, soft and contour to the face of a user better.

Figure 17:
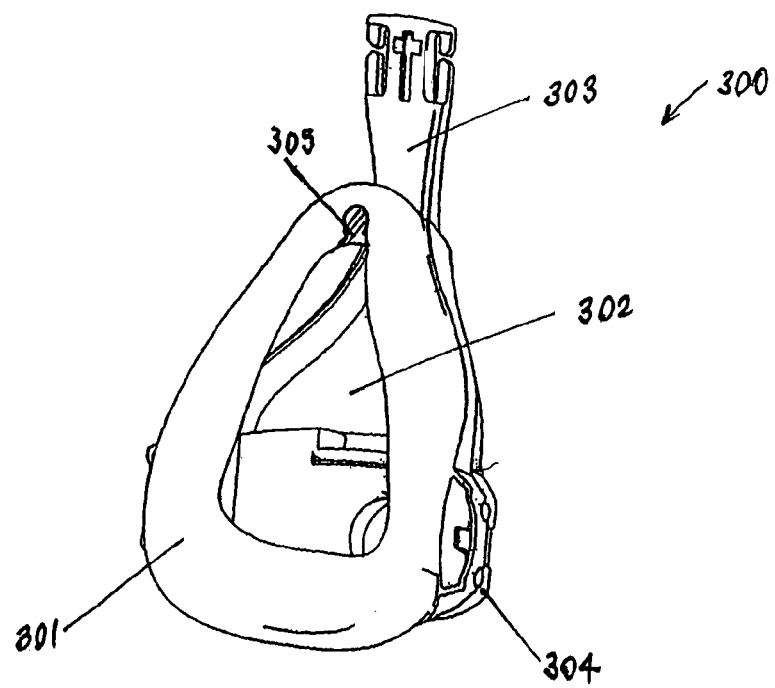
FIG. 17 is a back perspective view of a full face mask of FIG. 16.
Figure 18:
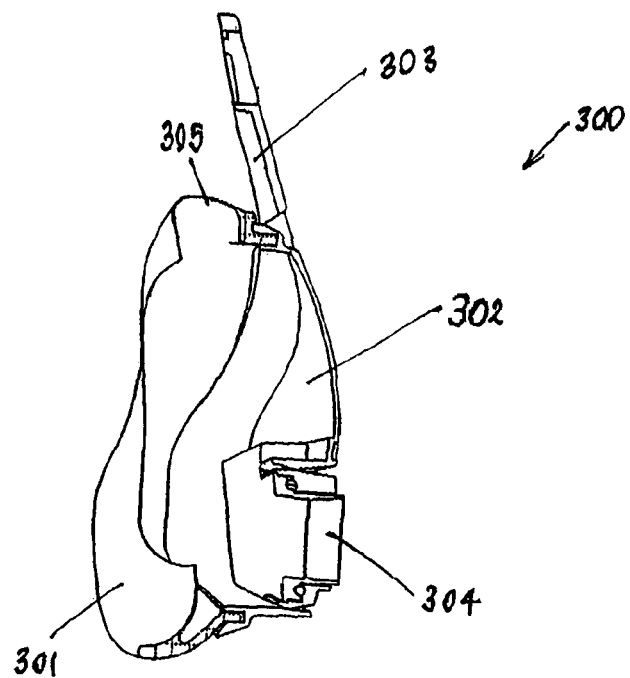
FIG. 18 is a cross-section through BB of the full face mask of FIG. 16.
Figure 19:
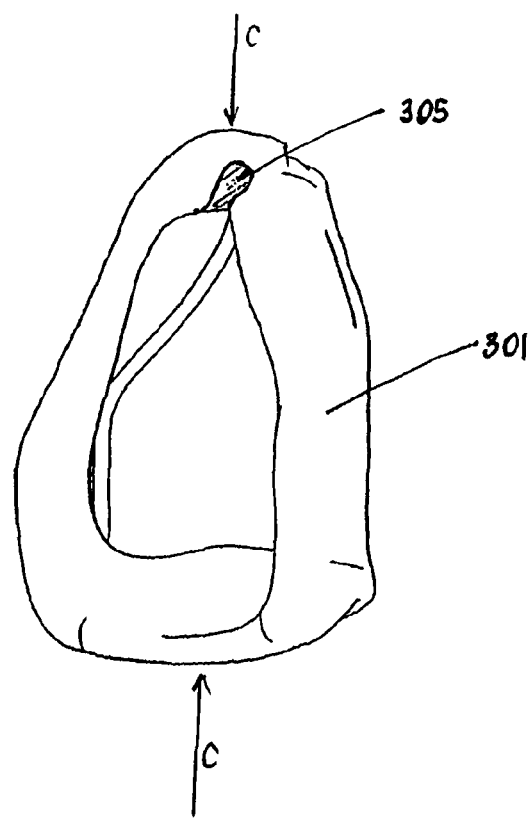
FIG. 19 is a perspective view of the outer sealing member of the full face mask of FIG. 16 in isolation, where the thin nasal bridge region is particularly shown.

The outer cushion as described above may be manufactured in a number of ways. Firstly, the outer cushion may be manufactured in a two component moulding process. For example, with the full face mask as shown in FIGS. 16 and 17 the outer cushion (shown in FIG. 23) might be manufactured by injection moulding in a plastics material, such as silicon. The mould for the outer cushion may have a deep area for the substantially rigid periphery but shallow areas for the softer areas. During the moulding process a harder grade plastics, such as a harder grade silicone "hard silicone", such as one of shore A 60 to 80, would be injected at the top of the mould, the hard silicone would flow into the mould and naturally flow into the deep area. Then after a predetermined time, possibly as short as a few seconds, to allow from some setting of the hard silicone, a soft silicone, for example, one with a grade of shore A 3 to 40 would be injected centrally and the silicone would flow up to over or around the hard silicone then into the rest of the mould.

In another form the moulding of the outer cushion may be completed by two moulding machines where the hard part of the cushion is moulded in one machine and the soft part moulded in another.

Figure 23:
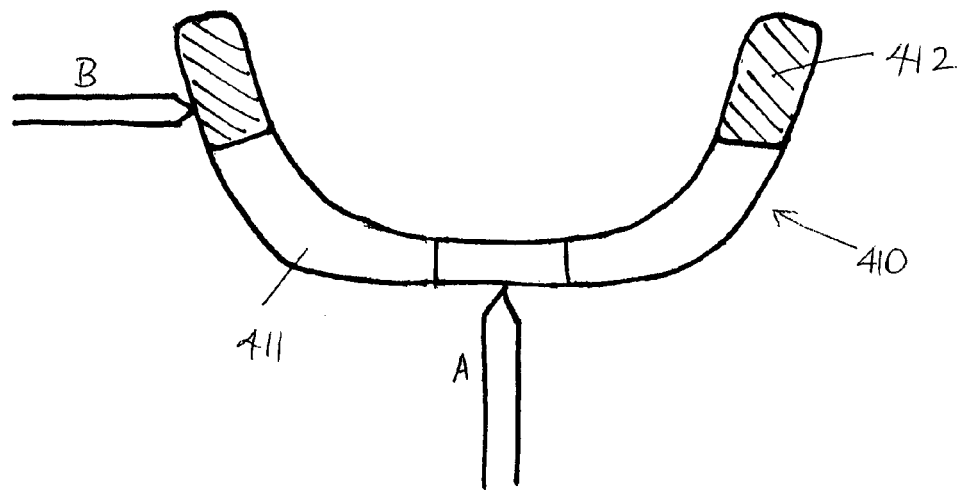
FIG. 23 is a cross-section of a simple sealing interface of a further embodiment of the present invention, showing areas where the sealing interface may be injection moulded.

Alternatively, a single moulding machine may be used where the machine has a single cavity and two or more injection points. For example, as shown in FIG. 23 the outer cushion 410 has its soft part 411 injected at point A, central to the cushion 410. As discussed above the soft part may be any appropriate plastics material, such as silicone. A second injection point would be from the side B where the hard or substantially rigid part 412 is injected into a mould; the injected "hard material" flows over the soft part 411 and forms the top rigid part 412.

Alternatively, the outer cushion may be formed in one moulding machine that has more than one cavity. For example one of the soft or hard part is injection moulded in a first cavity, then this part is removed from the first cavity and put into a second cavity where the other hard or soft part is injection moulded. If necessary the first part to be moulded may be moved by a robot or the like. Alternatively, the machine may include a rotating mould that enables different mould to be placed about the part.

In other forms the hard plastic used in the outer cushion may be made from a cheaper hard plastics material, for example, of shore D 40 to 80 hardness. Alternatively, the hard plastics material may be a thermoplastic polycarbonate nylon, a thermoplastic rubber, for TM example, KRATON™, or other appropriate material.

In yet other forms the substantially rigid periphery may include barbs or protrusions that would assist in a snap or friction engagement when the outer cushion is attached to the body or base of the patient interface.

Figure 24:
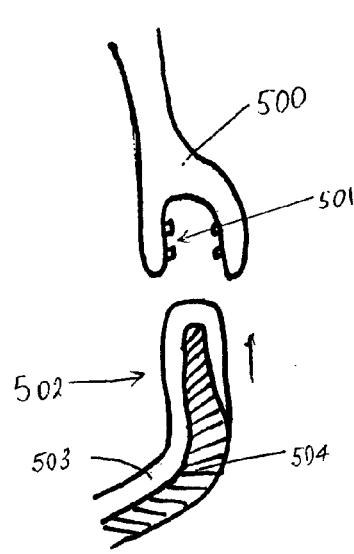
FIGS. 24 to 26 are three diagrams of different embodiments of a sealing interface fitting with a hollow body of a patient interface where the sealing interface includes a rigid periphery or section.
Figure 25:
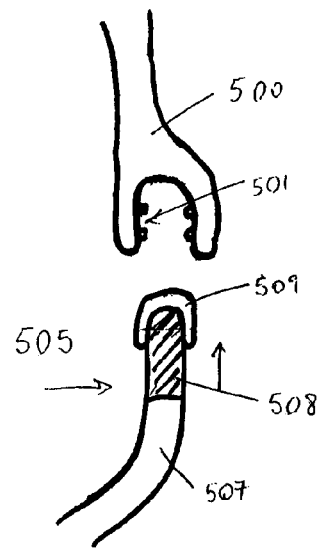
Figure 26:
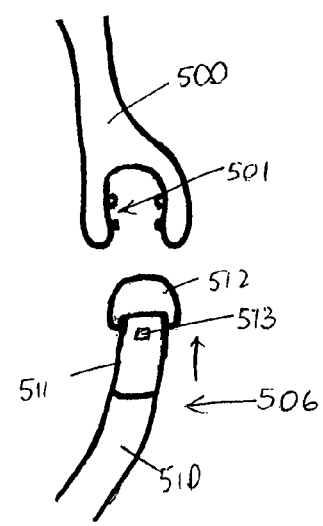

Yet other forms of the outer cushion of the present invention are shown in FIGS. 24 to 26. In FIG. 24 the hollow body or base of the patient interface 500 includes protrusions 501. The outer cushion 502 is push fit to the base for use. The outer cushion includes a soft part 503 and a rigid part 504 (made from materials as described above). Here the soft part has been moulded to extend over the rigid part such that when the cushion is fitted to the base 500 the soft parts are compressed by the protrusions.

FIGS. 25 and 26 show similar but slightly differing embodiments of an outer cushion 505, 506 where the top edge of the cushion is covered in a soft material to add in the friction fit of the cushion 505, 506 to the base 500. In FIG. 25 the outer cushion 505 has a lower soft part, a substantially rigid periphery 508 with a soft cap 509 over the top part of the rigid periphery 508. In FIG. 26 the outer cushion 505 has a lower soft part 510 a substantially rigid periphery 511 with a similar soft cap 512 moulded over the top part of the periphery 511. Here the cap 512 is keyed into an aperture 513 in the periphery 511 to ensure the cap 512 remains attached to the periphery 511 after the moulding process is completed.

Therefore with any of the embodiments of the outer cushion described above the bond between the soft part and rigid parts may be mechanical (with a keying such as is shown in FIG. 26) or simply where there is a chemical bonding of the materials after moulding of the parts together.

The invention claimed is:

1. A breathing assistance apparatus for use with delivery of respiratory gases to a patient comprising: a patient interface, having a body section adapted to cover the nose, or nose and mouth of said patient, a sealing interface, including at least an outer sealing member, said outer sealing member having a periphery that is attachable to said body section in a sealing manner, said periphery being substantially rigid compared to the remainder of said outer sealing member, wherein said outer sealing member is adapted to substantially seal around the facial contours of said patient providing a sealed fluid communication to the respiratory tract of said patient.

2. A breathing assistance apparatus according to claim 1 wherein said body section includes a ridge to receive said periphery of said sealing interface.

3. A breathing assistance apparatus according to claim 2 wherein said ridge includes protrusions that assist in the friction engagement of said sealing interface to said body section.

4. A breathing assistance apparatus according to claim 1 wherein said periphery includes protrusions that assist in a friction or snap engagement of said sealing interface to said body section.

5. A breathing assistance apparatus according to claim 1 wherein said patient interface is a full face mask.

6. A breathing assistance apparatus according to claim 1 wherein said patient interface is a nasal mask.

7. A breathing assistance apparatus according to claim 1 wherein said outer sealing member has a substantially thin section in at least its nasal bridge region, said thin section being substantially thinner than the remainder of said outer sealing member.

8. A breathing assistance apparatus according to claim 1 wherein said outer sealing member includes a second thin section in the region where said outer sealing member rests against the chin of said patient in use, said second thin section being substantially thinner than the remainder of said outer sealing member.

9. A breathing assistance apparatus according to claim 1 wherein said outer sealing member has a substantially thin section in at least its nasal bridge region, said thin section being substantially thinner than the remainder of said outer sealing member.

10. A breathing assistance apparatus according to claim 1 wherein said sealing interface includes an inner sealing member fittable into said outer sealing member.

11. A breathing assistance apparatus according to claim 9 wherein said inner sealing member has a cut out region in the nasal bridge region.

12. A breathing assistance apparatus according to claim 9 wherein said inner sealing member has a cut out region in the cheek region.

13. A breathing assistance apparatus according to claim 9 wherein said inner sealing member has a cut out region in the upper lip region.

14. An interface capable of delivering gases to a user comprising: a body adapted to cover said user's nose or nose and mouth of said user, an outer sealing member having a face seal portion that is soft and flexible which in use substantially seals against the user's face, said outer sealing member having an outer portion that follows the outer periphery of said outer sealing member, said outer portion being harder than said face seal portion and which in use attaches to said body.

15. An interface according to claim 14 where said outer portion has protrusions that assists in engagement of said outer sealing member with said body.

16. An interface according to claim 14 where said outer portion has a soft layer covering.

17. An interface according to claim 14 where an inner cushion is fittable into said outer sealing member.

* * * * *